United States Patent [19]

Jacquet et al.

[11] Patent Number: 4,767,750
[45] Date of Patent: Aug. 30, 1988

[54] TOPICAL COMPOSITIONS INTENDED FOR SKIN TREATMENT CONTAINING SALICYLIC ACID DERIVATIVES

[75] Inventors: Bernard Jacquet, Antony; Jean L. Leveque, Montfermeil; Michel Hocquaux; Didier S. Leger, both of Paris, all of France

[73] Assignee: L'Oreal, Paris, France

[21] Appl. No.: 860,434

[22] Filed: May 7, 1986

[30] Foreign Application Priority Data

May 7, 1985 [FR] France .................. 85 06953

[51] Int. Cl.⁴ ............................. A61K 31/60
[52] U.S. Cl. ................... 514/159; 514/852; 514/859; 514/863
[58] Field of Search ........................ 514/159

[56] References Cited

U.S. PATENT DOCUMENTS 4,244,948 1/1981 Boghosian et al. ............ 514/159
4,404,198 9/1983 Kelley ..................... 514/159

FOREIGN PATENT DOCUMENTS 0038192 10/1981 European Pat. Off. .
0055635 7/1982 European Pat. Off. .
0124905 11/1984 European Pat. Off. .
2172868 10/1973 France .
2213068 8/1974 France .
2144326A 3/1985 United Kingdom .

OTHER PUBLICATIONS

Chemical Abstracts, vol. 78, No. 9, Mar. 5, 1973, p. 37, Ref. No. 52753c.
Chemical Abstracts, vol. 75, No. 15, Oct. 11, 1971, p. 292, Ref. No. 98285t.

*Primary Examiner*—Leonard Schenkman
*Attorney, Agent, or Firm*—Fleit, Jacobson, Cohn & Price

[57] ABSTRACT

Topical compositions intended for skin treatment and based on salicylic acid derivatives.

The invention relates to topical compositions with a keratolytic and/or comedolytic effect, containing, in a carrier which is suitable for application to skin, at least one compound corresponding to the formula I:

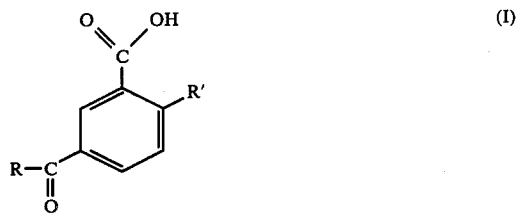

in which R denotes a linear, branched or cyclized saturated aliphatic chain containing from 3 to 11 carbon atoms, an unsaturated chain containing from 3 to 17 carbon atoms and containing one or more conjugated or unconjugated double bonds, these various substituents being optionally substituted by one or more halogen atoms, by one or more trifluoromethyl groups, by one or more hydroxyl groups in free form or esterified with an acid containing from 1 to 6 carbon atoms or by a carbonyl group which is free or esterified with a lower alcohol containing from 1 to 6 carbon atoms, R' denotes a hydroxyl group or an ester group of formula:

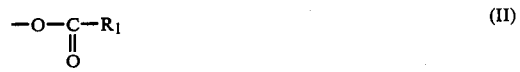

where $R_1$ denotes a saturated or unsaturated aliphatic group containing from 1 to 18 carbon atoms.

11 Claims, No Drawings

TOPICAL COMPOSITIONS INTENDED FOR SKIN TREATMENT CONTAINING SALICYLIC ACID DERIVATIVES

The present invention relates to the use of salicylic acid derivatives in topical compositions intended for the treatment of skin in the field of cosmetology and dermopharmacy.

In cosmetics, products having keratolytic activity, especially in antidandruff products, compositions for treating dry skins, beauty masks and for what are known as "peeling" processes, are sought after. While permitting the removal of dead or hyperkeratinized skins, these products must not give rise to any inflammation.

The use of keratolytic and comedolytic products is also of great interest in dermopharmacy, especially in the treatment of diseases affecting the horny layer in man or animals, such as verrucas, acne, eczema, psoriasis, ulcers, and the like.

Among the diseases of the skin, acne is one of the diseases which most frequently and in various degrees affects the juvenile population aged between 15 and 30. Acne is due essentially to the increase, at the time of puberty, in the production of androgens such as testosterone, which stimulate the sebaceous glands, increasing sebum production. At the same time, a hyperkeratinization of the follicular duct is observed, which gives rise in the pilosebaceous follicle to a rich nutrient environment for bacterial flora and which, in particular, promotes the proliferation of diphtheroid anaerobic bacteria such as *Propionibacteria (acnes, granulosum, avidum)*.

While the use of keratolytic products is of interest in the treatment of acne, the search continues for means which at the same time can provide an antibacterial effect in respect of the abovementioned strains of bacteria which are responsible for the subsequent appearance of inflammation.

Salicylic acid is known for its keratolytic properties and is generally employed as a desquamating agent against acne. However, it has the disadvantage of, on the one hand, being required in large quantities, which can give rise to skin irritations and, on the other hand, of not being bacteriostatic with regard to the principal bacteria in the acne spectrum, such as *Propionibacterium acnes*.

The Applicant has now found new salicylic acid derivatives substituted in the 5-position, which surprisingly have a keratolytic activity greater than that of salicylic acid, at markedly lower concentrations, and a specific and effective bacteriostatic activity towards the chief bacteria associated with acne.

The subject of the present application is therefore new compositions intended to be used in cosmetics or in dermopharmacy and having bacteriostatic and keratolytic properties.

Another subject of the invention consists in the use and in the preparation of such a composition, based on keratolytic and/or bacteriostatic compounds as defined above.

Other subjects of the invention will become apparent from the reading of the description and of the examples which follow.

The compounds used in accordance with the invention correspond to the general formula:

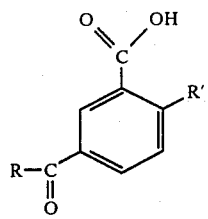
(I)

in which R denotes a linear, branched or cyclized saturated aliphatic chain containing from 3 to 11 carbon atoms, an unsaturated chain containing from 3 to 17 carbon atoms and containing one or more conjugated or unconjugated double bonds, the abovementioned chains being optionally substituted by one or more halogen atoms or by trifluoromethyl groups, by one or more hydroxyl groups in free form or esterified by an acid containing from 1 to 6 carbon atoms, or by a carboxyl group, free or esterified by a lower alcohol containing from 1 to 6 carbon atoms, these various groups being optionally simultaneously present in the said substituents.

R' denotes a hydroxyl group or an ester group of formula:

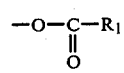
(II)

where $R_1$ is a saturated or unsaturated aliphatic group containing from 1 to 18 carbon atoms.

The compounds which are more especially preferred are those in which R' denotes a hydroxyl group and R an alkyl group containing from 3 to 11 carbon atoms.

Other compounds which are especially interesting are those in which R denotes a chain derived from linoleic, linolenic or oleic acid.

Another group of especially preferred compounds consists of the compounds in which R denotes an alkyl chain containing from 3 to 11 carbon atoms and bearing a free, esterified or salified carboxylic group, and R' denotes a hydroxyl group.

Some of these compounds are known. These new or known compounds may be prepared by an acylation reaction of the Friedel and Crafts type, between an acid chloride and the methyl ester of salicylic acid, in the presence of a catalyst such as, preferably, anhydrous aluminium chloride. Such reactions have been described, in particular, by Olah, "Friedel-Crafts and Related Reactions" Interscience Publishers, New York 1963-1964, and by Gore, Chem. Rev. 55, 229-281 (1955), according to the following reaction scheme:

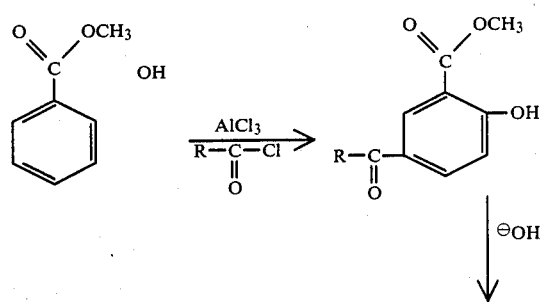

-continued

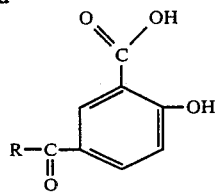

Antibacterial Activity

The bacteriostatic activity of these compounds has been determined, using conventional methods, on the following strains: P. acnes, granulosum, avidum and Staphylococcus epidermidis.

These strains have a sensitivity towards erythromycin (reference antibiotic) which is comparable to that outlined in J. Leyden's work (J. Am. Acad. Dermatol. 8,1,41-5, 1983) and may be considered as being representative of the bacterial population normally to be found in cases of acne. The solvents which can be used are water, a 20/80 mixture of water and ethanol, dimethyl sulphoxide (DMSO), and a 40/10/50 mixture of water, ethanol and propylene glycol. The products to be investigated are dissolved in one of these solvents at a concentration of 4 mg/ml. Some light-sensitive products are dissolved under a yellow light.

Two methods have been employed:

(1) A qualitative method consisting in depositing 50 and 200 μg of product on a paper disc or in a microcup cut from inoculated agar. 4 to 5 days after inoculation, any inhibition zone which may be present around the disc or the microcup is measured and recorded. Where the result is negative, the product is considered inactive.

(2) A quantitative method, consisting in the use of the conventional method of successive dilutions by a half and using the solvent at a fixed dosage of 5% in each microcup. In this way, the M.I.C. (minimum inhibiting concentration) for the product has been determined, expressed in μg/ml and corresponding to the first microcup where bacterial growth is appreciably reduced compared to the control bacteria. Erythromycin has been used as a positive control in each experiment.

These results have demonstrated good antibacterial activity of the compounds according to the invention against the acne spectrum.

Comedolytic Activity

Comedolytic activity has been determined by means of tests on the Rhino mouse, using Lowe's method, and the histological method of Bonne et al.

These tests are carried out on the skin of the Hairless Rhino mouse, recommended as a model for screening comedolytic agents by Van Scott in 1972 and based on the histological picture. This method has been adopted by Bonne, with a recommendation that the test be made quantitative. In fact, in the Rhino mouse, the skin surface has cystic formations whose narrow orifice d, in its ratio to the diameter of the cyst D, defines, according to Bonne, a characteristic "comedonian profile". In the dorsal and interscapular region, the radio d/D, close to 0.4 to 0.7 in the control, is increased after topical application of the substance to be tested, as a solution, to $r = d/D \geq 1$ 15 male or female Hairless Rhino mouse, aged 2 and a half months at the beginning of the experiment were divided into three groups:

The first group was treated with an acetone solution of the substance to be investigated, at the required concentration. 200 μl of solution were applied to the back, on 5 consecutive days weekly, for 3 weeks.

The second group was treated with an acetone solution of the reference product at a given concentration.

The third group was treated with acetone.

24 hours after the last application, the mice were sacrificed by dislocation of the cervical vertebrae. Two specimens of dorsal skin were taken from the treated region.

Bonne's histological technique consists in fixing by the Karnovsky method, post-fixing in anhydrous osmium tetroxide, and then embedding in Epon. The blocks are cut into sections 2 μm thick. The sections are stained with Toluidine Blue and inspected under the microscope. The measurement of d (comedo opening) and D (comedo diameter) is carried out by means of a semiautomatic image analyser.

The second biopsy is treated using Lowe's technique. It is placed in a 0.5% strength solution of acetic acid at 4° C. overnight. The epidermis is separated from the dermis, dehydrated and mounted between a slide and cover slip in Aquamount. The mean surface area of the comedones is estimated by means of the image analyser.

The topical compositions with a keratolytic action according to the invention are essentially characterized in that they contain, in a carrier which is suitable for application to the skin, at least one compound corresponding to the formula I as defined above, in sufficient proportions to produce the desired keratolytic and/or comedolytic effect.

The proportions are preferably between 0.1 and 30% by weight relative to the total weight of the composition.

The compositions may be presented particularly in the form of gel, cream, lotion or stick.

They may contain water, solvents compatible with the skin, such as the lower $C_1$-$C_4$ alcohols, such as ethanol, isopropanol, and polyalcohols such as propylene glycol and glycerine, these solvents being present in proportions of 5 to 99% by weight.

These compositions may also contain thickeners, softeners, superfatting agents, emollients, wetting agents, surface-active agents, preserving agents, antifoams, sunscreens, oils, waxes, colorants and/or pigments intended to colour the skin or the composition itself, preserving agents, and any other ingredient which is usually employed in compositions intended for topical application.

Compositions which are especially preferred are creams or milks comprising, in addition to the compounds defined above, fatty alcohols, oxyethylenated or polyglycerolated fatty alcohols, fatty acid esters, natural or synthetic oils, and waxes.

A preferred embodiment of the invention consists of creams, gels and lotions intended for makeup, for treating dry skins, for masks or for "peeling" compositions.

Another form of cosmetic application consists of antidandruff lotions.

The pharmaceutical compositions which are intended for the treatment of skin diseases, and which are particularly preferred, are those containing compounds of formula I in which:

R' denotes a hydroxyl group, and

R denotes a linear or branched alkyl chain containing from 3 to 11 carbon atoms, optionally substituted by one or more halogen atoms or trifluoromethyl groups, or hydroxyl or carboxyl groups which may be esterified.

Another subject of the invention is the use of a compound of formula I as defined above in the preparation of pharmaceutical compositions intended for the treatment of acne.

In the treatment of acne, the compositions according to the invention are applied once to twice daily in sufficient quantities, preferably of between 2 and 10 mg/cm$^2$ skin, on all the areas to be treated, and for a period which may range from 1 week to 3 months.

According to one embodiment, the compounds according to formula (I) may be used in combination with other derivatives which are generally employed in the treatment of acne, such as benzoy, peroxide, macrolides such as erythromycin, clindamycin and lincomycin, the carotenoids, azulene, tetracyclines, and retinoids.

The compositions according to the invention also yield good results in the treatment of hyperkeratoses and are used in forms similar to those recommended for the treatment of acne.

The following examples are intended to illustrate the invention without, however, being of a limiting nature.

EXAMPLE OF PREPARATION A

Preparation of 5-n-Octanoylsalicylic Acid (a) 180 g of aluminium chloride are added to 450 cm$^3$ of anhydrous $CS_2$. The stirred suspension is kept at 5°–10° C. A mixture of 68.5 g of methyl salicylate and of 122 g of capryloyl chloride dissolved in 150 cm$^3$ of anhydrous $CS_2$ is added dropwise. The mixture is stirred for 16 hours at ambient temperature.

The reaction solution is poured onto 1.5 liters of ice and water containing 75 ml of concentrated hydrochloric acid and is then extracted with ether. The organic phase, washed with a saturated sodium chloride solution, is dried over sodium sulphate and is then evaporated. 100 g of the methyl ester of 5-n-octanoylsalicylic acid are obtained in 80% yield. The melting point is 61° C. after recrystallization from petroleum ether. Thin-layer chromatography on silica gel, using $CH_2Cl_2$ as eluent, gives an $R_f$ value of 0.8.

(b) 80 g of the methyl ester of 5-n-octanoylsalicylic acid are suspended in 375 cm$^3$ of ethanol. 62.5 g of sodium hydroxide, dissolved in 750 cm$^3$ of $H_2O$ are added. The suspension is heated to 60° C. for 5 hours. After cooling, 130 cm$^3$ of concentrated hydrochloric acid are added. The white precipitate which is formed is filtered off, washed with $H_2O$, dried over $P_2O_5$, and recrystallized from 500 cm$^3$ of dichloromethane.

5-n-Octanoylsalicylic acid is obtained in 85% yield (65 g). The melting point is 115° C. Mass and NMR spectra and elemental analysis are consistent with the structure.

Elemental analysis:

|  |  | C | H | O |
|---|---|---|---|---|
| $C_{15}H_{20}O_4$ | calculated | 68.18 | 7.57 | 24.24 |
| M = 264 | found | 68.44 | 7.57 | 24.47 |

EXAMPLE OF PREPARATION B 5-(3,3-Dimethylbutyroyl)Salicylic Acid

The same method as that described in example A is used, starting with methylsalicylate and t-butylacetyl chloride. The ester yield is 70%, the acid yield is 80%. After recrystallization from toluene a melting point of 148° C. is obtained.

Elemental analysis:

|  |  | C | H | O |
|---|---|---|---|---|
| $C_{13}H_{16}O_4$ | calculated | 66.10 | 6.78 | 27.12 |
| M = 236 | found | 66.14 | 6.78 | 27.89 |

Mass and NMR spectra are consistent with the structure.

EXAMPLE OF PREPARATION C 5-(Cyclobutylcarboxy)Salicylic Acid

This compound is prepared using the method of example A by starting with methyl salicylate and cyclobutanecarboxylic acid chloride. The ester yield is 57%, the acid yield is 80%. The recrystallization is done in an $H_2O$/ethanol mixture, the melting point is 200° C.

Elemental analysis:

|  |  | C | H | O |
|---|---|---|---|---|
| $C_{12}H_{12}O_4$ | calculated | 65.48 | 5.45 | 29.09 |
| M = 220 | found | 65.26 | 5.48 | 29.19 |

Mass and NMR spectra are consistent with the structure.

EXAMPLE OF PREPARATION D 5-(3-Carboxypropionyl)Salicylic Acid

The method is as described in example A, starting with methyl salicylate and carbomethoxypropionyl chloride. The ester yield is 21%, the acid yield is 81%. The recrystallization in done in acetone. The melting point is 205° C.

Elemental analysis:

|  |  | C | H | O |
|---|---|---|---|---|
| $C_{11}H_{10}O_6$ | calculated | 55.46 | 4.20 | 40.33 |
| M = 238 | found | 55.38 | 4.38 | 39.95 |

Mass and NMR spectra are consistent with the structure.

EXAMPLE OF PREPARATION E 5-(8-Carboxyoctanoyl)Salicylic Acid

This compound is prepared as described in example A by starting with methyl salicylate and the chloride of the monomethyl ester of azelaic acid. The ester yield is 50%, and the acid yield is 85%. The recrystallization is done in a mixture of petroleum ether and acetone, the melting point is 152° C.

Elemental analysis:

|  |  | C | H | O |
|---|---|---|---|---|
| $C_{16}H_{20}O_6$ | calculated | 62.33 | 6.49 | 31.17 |
| M = 308 | found | 62.20 | 6.52 | 29.81 |

Mass and NMR spectra are consistent with the structure.

EXAMPLE OF PREPARATION F

5-(2-Propylpentanoyl)Salicylic Acid

This compound is prepared by a Friedel-Crafts reaction from salicylic acid and 2-propylpentanoyl chloride. The acid yield is 52%. The recrystallization is done in petroleum ether. The melting point is 118° C.

Elemental analysis:

|  |  | C | H | O |
|---|---|---|---|---|
| $C_{15}H_{20}O_4$ | calculated | 68.18 | 7.57 | 24.14 |
| M = 264 | found | 67.81 | 7.66 | 24.58 |

Mass and NMR spectra are consistent with the structure.

EXAMPLE OF PREPARATION G

2-Acetyloxy-5-n-Octanoylbenzoic Acid 1 g of 5-n-octanoylsalicylic acid is suspended in 15 ml of acetic anhydride. After addition of 2 drops of concentrated sulphuric acid the solution is heated to 100° C. for 15 minutes. The solution is poured onto 150 ml of crushed ice. After extracting with ether, washing the organic phase with the water, drying over sodium sulphate and evaporating, 1 g of a white crystalline product is obtained. The yield is 85%. The recrystallization is done from a 50/50 mixture of toluene and petroleum ether. The melting point is 130° C.

Elemental analysis:

|  |  | C | H | O |
|---|---|---|---|---|
| $C_{17}H_{22}O_5$ | calculated | 66.67 | 7.19 | 26.14 |
| M = 306 | found | 66.61 | 7.21 | 25.98 |

PHARMACOLOGICAL STUDY

The antibacterial activity was determined using *Propionibacterium acnes*. The results, obtained using the method described above, were as follows:

TABLE I

| | | | Minimum inhibiting concentration (μg/ml) | | |
| | | | *Propionibacterium acnes* | *Propionibacterium acnes* | ATCC |
| No | R | R' | PC 10 | PC 37 | 6919 |
|---|---|---|---|---|---|
| 1 | $CH_3-(CH_2)_{10}-$ | OH | 0.78/0.78 | 3.12/6.25 | 0.78/1.56 |
| 2 | $CH_3-(CH_2)_8-$ | OH | 0.09/0.39 | 0.19/0.39 | 0.19/0.78 |
| 3 | $CH_3-(CH_2)_6-$ | OH | 3.12/6.25 | 1.56/6.25 | 0.39/3.12 |
| 4 | $CH_3-(CH_2)_6-$ | $O-\underset{\underset{O}{\parallel}}{C}-CH_3$ | 3.12/6.25 | 6.25/12.5 | 3.12/12.5 |
| 5 | $CH_3-(CH_2)_4-$ | OH | 25/50 | 25/12.5 | 12.5/12.5 |
| 6 | $CH_3-(CH_2)_2-$ | OH | 3.12/25 | 25/50 | 25/50 |
| 7 | $(CH_3)_3C-CH_2-$ | OH | 3.12/12.5 | 25/50 | 25/25 |
| 8 | $(CH_3CH_2)_2CH-$ | OH | 50 | 100 | 100 |
| 9 | $(CH_3CH_2CH_2)_2CH-$ | OH | 25/1.56/25 | 25/6.25/6.25 | 25/1.56/25 |
| 10 | $HO-\underset{\underset{O}{\parallel}}{C}-(CH_2)_2-$ | OH | 100 | 100 | 100 |
| 11 | $HO-\underset{\underset{O}{\parallel}}{C}-(CH_2)_7-$ | OH | 100 | 100 | 100 |
| 12 | cyclopropyl- | OH | 50/50 | 25/50 | 25/50 |
| 13 | phenyl- | OH | 25 | 100/50 | 50/25 |

TABLE I-continued

| | | | Minimum inhibiting concentration (μg/ml) | | |
|---|---|---|---|---|---|
| No | R | R' | Propionibacterium acnes PC 10 | Propionibacterium acnes PC 37 | ATCC 6919 |
| 14 | ⟨benzyl⟩—CH$_2$— | OH | 200/50 | 100/100 | 100/100 |
| 15 | Salicylic acid | | 100/100 | 100/200 | 200 |

Salicylic acid is observed to have no appreciable effect on *Propionibacterium acnes*.

The antibacterial activity was also determined for some compounds using *Propionibacterium granulosum*, *Propionibacterium avidum* and two strains of *Staphylococcus epidermidis* (Table II).

TABLE II

| | | | Minimum inhibiting concentrations in μg/ml | | | |
|---|---|---|---|---|---|---|
| No | R = | R' = | Propionibacterium granulosum | Propionibacterium avidum | Staphylococcus epidermidis STE 3 | Staphylococcus epidermidis STE 6 |
| 1 | CH$_3$—(CH$_2$)$_{10}$— | OH | 1.56/3.12 | 3.12/0.78 | 12.5/1.56 | 12.5/1.56 |
| 2 | CH$_3$—(CH$_2$)$_8$— | OH | 1.56/1.56 | 1.56/6.25 | 3.12/3.12 | 3.12/6.25 |
| 3 | CH$_3$—(CH$_2$)$_6$— | OH | 5.25/12.5 | 3.12/25 | 50/50 | 50/50 |
| 4 | CH$_3$—(CH$_2$)$_6$— | —O—C(=O)—CH$_3$ | 25/6.25 | 25/1.56 | 50/50 | 50/100 |

These compounds exhibit good activity towards the strains of *Propionibacterium* (*acnes, granulosum* and *avidum*) involved in acne. Their activity is at its lowest in the case of compounds nos. 3 and 4 for strains of *Staphylococcus epidermidis*.

The antibacterial activity of two topical antiacne compositions containing 1 and 3% of 5-n-octanoylsalicylic acid was studied, using the tablet diffusion method in a mixture of ethanol and propylene glycol.

The values in Table III denote the inhibition regions, in mm.

TABLE III

| MICROORGANISMS | 1% composition | 3% composition |
|---|---|---|
| PROPIONIBACTERIUM ACNES | 17.5 | 36.6 |
| PROPIONIBACTERIUM GRANULOSUM | 12.2 | >40 |
| STAPHYLOCOCCUS AUREUS | 21.7 | 26 |
| SARCINA LUTEA | 13.6 | 20 |
| MICROCOCCUS FLAVUS | 17.2 | 22 |
| STAPHYLOCOCCUS EPIDERMIDIS | 13.3 | 16.3 |
| MICROCOCCUS LUTEUS | 19.5 | 25.3 |

COMEDOLYTIC ACTIVITY

This is measured using Rhino mice as described above. The results are shown in the following Tables.

TABLE IV

| | Lowe's technique | |
|---|---|---|
| Groups of animals (5 animals) | | Mean surface area of the comedones, μm$^2$ |
| 1 | Acetone controls (5 animals) | 250 06 |
| | 3% 5-n-octanoyl-salicylic acid (5 animals) | 70 13 |
| | 6% benzoyl peroxide* (5 animals) | 83 32 |
| 2 | Acetone controls (5 animals) | 110 60 |
| | 3% 5-n-octanoyl-salicylic acid (5 animals) | 38 48 |
| | 6% benzoyl peroxide (5 animals) | 79 30 |

*3% benzoyl peroxide produces no significant results.

In analogous manner to that described above, the comedolytic activity was determined for 5% 5-n-dodecanoylsalicylic acid, which is greater than the control, and for 5% 5-n-decanoyl salicylic acid, which is found to be much greater than the same control.

TABLE V

| | Histological technique | | | |
|---|---|---|---|---|
| Group of animals | (5 animals) | d μm | D μm | $r = \frac{d}{D}$ |
| 1 Acetone controls | (5 animals) | 78.16 | 113.92 | 0.800 |
| 3% 5-n-octanoyl-salicylic acid | (5 animals) | 56.36 | 64.49 | 0.975 |
| 6% benzoyl peroxide | (5 animals) | 75.88 | 85.09 | 0.966 |
| 2 Acetone controls | (5 animals) | 61.85 | 100.36 | 0.658 |
| 3% 5-n-octanoyl-salicylic acid | (5 animals) | 50.97 | 43.35 | 1.323 |

It is found that the comedolytic activity of the compound tested at 3% strength in acetone is similar to that of 6% benzoyl peroxide in the same solvent, according to the test using Rhino mice.

EXAMPLES OF COMPOSITION

The following compositions were prepared:

EXAMPLE 1

Antiacne gel

The following composition was prepared:

| | |
|---|---|
| 5-n-Octanoylsalicylic acid | 3 g |
| 90° ethanol | 50 g |
| Propylene glycol | 45.5 g |
| Klucel HF (soluble hydroxypropylcellulose sold by Hercules) | 1.5 g |

EXAMPLE 2

Antiacne cream
The following composition is prepared:

| | |
|---|---|
| Autoemulsifiable glycerol stearate sold under the name "Gelot 64" by Gattefosse | 15 g |
| Palm oil with transesterified polyethylene glycol, sold under the name "Labrafil M 2130 CS" by Gattefosse | 8 g |
| Perhydrosqualene | 10 g |
| Polyethylene glycol 400 | 8 g |
| Ethylenediaminetetraacetic acid | 0.05 g |
| Keltrol (xanthane gum-based polysaccharide, sold by Kelco) | 0.25 g |
| 5-n-Octanoylsalicylic acid | 2 g |
| Water q.s. | 100 g |

EXAMPLE 3

Antiacne lotion
The following composition is prepared:

| | |
|---|---|
| 5-n-Octanoylsalicylic acid | 2 g |
| 90° ethanol | 60 g |
| Propylene glycol | 10 g |
| Glycerine | 3 g |
| Polyethylene glycol 400 | 3 g |
| Water q.s. | 100 g |

EXAMPLE 4

Antiacne hiding stick
The following composition is prepared:

| | |
|---|---|
| Carnauba wax | 6 g |
| Ozokerite | 6 g |
| Cetyl alcohol | 1 g |
| Lanolin | 6 g |
| Antioxidant agent | 0.1 g |
| Titanium oxide | 20 g |
| Yellow and red iron oxide | 4.5 g |
| 5-n-Octanoylsalicylic acid | 1.5 g |
| Perhydrosqualene q.s. | 100 g |

This composition is used as a hiding product for the treatment of acne.

The compositions of Examples 1 to 4 above are used in 1 or 2 applications daily on the areas affected by acne, for a period of 1 week to 3 months.

EXAMPLE 5

Antiacne gel
The following composition is prepared:

| | |
|---|---|
| 5-n-Dodecanoylsalicylic acid | 3 g |
| Ethanol | 58.5 g |
| 2-Octyldodecanol | 37 g |
| Soluble hydroxypropylcellulose | 1.5 g |

EXAMPLE 6

Antiacne gel
The following composition is prepared:

| | |
|---|---|
| 5-n-Decanoylsalicylic acid | 3 g |
| Ethanol | 58.5 g |
| Propylene glycol methyl ether | 37 g |
| Soluble hydroxypropylcellulose | 1.5 g |

The antibacterial activity of this composition was determined for two strains of Propionibacterium acnes. The minimum inhibiting concentration (µg/ml), analogous to Table 1, is 2.34/2.34 for Propionibacterium acnes PC 37 and 4.68/2.34 for ATCC 6919.

EXAMPLE 7

Antiacne gel
The following composition is prepared:

| | |
|---|---|
| 5-n-Dodecanoylsalicylic acid | 5 g |
| Ethanol | 57.5 g |
| Propylene glycol methyl ether | 36 g |
| Soluble hydroxypropylcellulose | 1.5 g |

The antibacterial activity of this composition was determined for the strains of Propionibacterium acnes PC37 and ATCC 6919. The minimum inhibiting concentration (µg/ml), analogous to Example 6, is 0.97/1.95 for PC37 and 0.48/3.9 for ATCC 6919.

EXAMPLE 8

Antiacne gel
The following composition is prepared:

| | |
|---|---|
| 5-n-Decanoylsalicylic acid | 3 g |
| Ethanol | 58.5 g |
| Propylene glycol methyl ether | 37 g |
| Soluble hydroxypropylcellulose | 1.5 g |

The antibacterial activity of this composition was determined for the two strains of Propionibacterium acnes PC 37 and ATCC 6919. The minimum inhibiting concentration (µg/ml), analogous to Example 6, is 1.17/2.34 for PC 37 and 2.34/4.68 for ATCC 6919.

The antibacterial activity of the three antiacne compositions according to Examples 6 to 8 was studied using the tablet diffusion method in an ethanol/propylene glycol mixture.

The values in Table VI denote the inhibition regions, in mm.

TABLE VI

| MICROORGANISMS | Composition according to Example 6 | Composition according to Example 7 | Composition according to Example 8 |
|---|---|---|---|
| PROPIONIBACTERIUM ACNES | 39.1 | 40 | >40 |
| PROPIONIBACTERIUM GRANULOSUM | 30.6 | 30 | 32.8 |
| STAPHYLOCOCCUS AUREUS | 25.3 | 22.8 | 28.8 |
| SARCINA LUTRA | 16.6 | 18.3 | 20.8 |
| STAPHYLOCOCCUS EPIDERMIDIS | 19.6 | 21.5 | 20.6 |
| MICROCOCCUS LUTEUS | 13 | 12 | 30.1 |

EXAMPLES FOR THE TREATMENT OF HYPERKERATOSIS

EXAMPLE 9

Ointment for the treatment of hyperkeratosis

| 5-n-Octanoylsalicylic acid | 5 g |
|---|---|
| Vaseline | 95 g |

EXAMPLE 10

Ointment for the treatment of hyperkeratosis

| 5-n-Octanoylsalicylic acid | 5 g |
|---|---|
| Vaseline | 47.5 g |
| Polytetrahydrofuran dimethyl ether with a viscosity of 22 cP | 47.5 g |

EXAMPLE 11

Ointment for the treatment of hyperkeratosis

| 5-n-Octanoylsalicylic acid | 10 g |
|---|---|
| Vaseline | 45 g |
| Cosbiol (perhydrosqualene) | 45 g |

EXAMPLE 12

Stick for the treatment of hyperkeratosis

| Micronized 5-n-octanoylsalicylic acid | 5 g |
|---|---|
| Paraffin wax | 30 g |
| Liquid paraffin | 30 g |
| Vaseline | 35 g |

These compositions are applied once to twice daily to the areas affected and for a treatment period of 1 week to 2 months.

What is claimed is:

1. Topical dermopharmaceutical and/or cosmetic composition in the form of a cream, milk, gel, lotion, stick or beauty mask with a keratolytic and/or comedolytic effect, containing in a carrier which is suitable for application to skin, an effective amount of at least one compound corresponding to the formula I

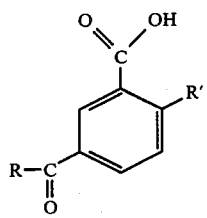

in which R denotes a linear, branched or cyclized saturated aliphatic chain containing from 3 to 11 carbon atoms, an unsaturated chain containing from 3 to 17 carbon atoms, and containing one or more conjugated or unconjugated double bonds, the above mentioned chains being unsubstituted or substituted by one or more halogen atoms, by one or more trifluoromethyl groups, by one or more hydroxyl groups in free form or esterified with an acid containing from 1 to 6 carbon atoms or by a carboxy group, free or esterified with a lower alcohol containing from 1 to 6 carbon atoms, R' denotes a hydroxyl group or an ester group of formula:

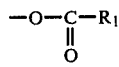

where $R_1$ denotes a saturated or unsaturated aliphatic group containing from 1 to 18 carbon atoms.

2. Composition according to claim 1, wherein the compounds of formula I are compounds in which R' denotes a hydroxyl group and R an alkyl group containing from 3 to 11 carbon atoms.

3. Composition according to claim 1, wherein compounds of formula I in which R' denotes a hydroxyl group and R denotes an alkyl radical containing from 3 to 11 carbon atoms bearing a free, esterified or salified carboxylic group are employed.

4. Composition as defined in claim 1, containing from 0.1 to 30% of the active substance of formula I.

5. Composition according to claim 1 in the form of a cream based on fatty alcohols, oxyethylenated or polyglycerolated fatty alcohols, fatty acid esters, natural or synthetic oils or waxes or petroleum jelly.

6. A cosmetic treatment of skin comprising applying to the skin a composition as defined in claim 1 in the form of makeup or a beauty mask.

7. A composition in the form of a cream, milk, gel, lotion, stick or beauty mask for the treatment of diseases affecting the horny layer in man or animals comprising at least one compound corresponding to the formula I

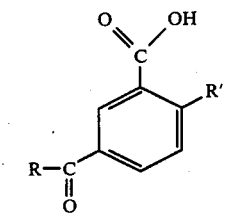

wherein R' denotes a hydroxyl group and R denotes an alkyl radical containing from 3 to 11 carbon atoms in an amount of 0.1 to 30% by weight in a carrier which can be applied to the skin.

8. Composition according to claim 7, containing in combination with the compound of formula (I), other active derivatives which are benzoyl peroxide, macrolides, tetracyclines, carotenoids, azulenes, retinoids or mixtures thereof.

9. Composition according to claim 7, containing additionally thickeners, softeners, superfatting agents, surface-active agents, preserving agents, antifoams, sunscreens, oils, waxes, colorants and/or pigments intended to colour the composition or skin, or preserving agents.

10. A method of treating skin comprising applying to the skin a composition as defined in claim 1.

11. A method of treating dandruff comprising topically applying a composition containing in a carrier which is suitable for application to skin, an anti-dandruff amount of at least one compound corresponding to the formula I:

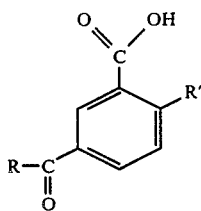 (I)

in which R denotes a linear, branched or cyclized saturated aliphatic chain containing from 3 to 11 carbon atoms, an unsaturated chain containing from 3 to 17 carbon atoms, and containing one or more conjugated or unconjugated double bonds, the above mentioned chains being optionally substituted by one or more halogen atoms, by one or more trifluoromethyl groups, by one or more hydroxyl groups in free form or esterified with an acid containing from 1 to 6 carbon atoms or by a carboxyl group, free or esterified with a lower alcohol containing from 1 to 6 carbon atoms, R' denotes a hydroxyl group or an ester group of formula:

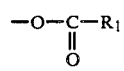 (II)

wherein $R_1$ denotes a saturated or unsaturated aliphatic group containing from 1 to 18 carbon atoms.

* * * * *